US00PP12079P2

(12) United States Plant Patent
Flemer, III

(10) Patent No.: US PP12,079 P2
(45) Date of Patent: Sep. 4, 2001

(54) *VIBURNUM DENTATUM* PLANT NAMED 'OCTOBER GLORY'

(75) Inventor: William Flemer, III, Allentown, NJ (US)

(73) Assignee: Treesearch, Allentown, NJ (US)

( * ) Notice: Subject to any disclaimer, the term of this patent is extended or adjusted under 35 U.S.C. 154(b) by 0 days.

(21) Appl. No.: 09/247,271

(22) Filed: Feb. 10, 1999

(51) Int. Cl.[7] ..... A01H 5/00

(52) U.S. Cl. ..... Plt./226

(58) Field of Search ..... Plt./226

(56) References Cited

PUBLICATIONS

Huxley, A., Griffiths, M., Levy, M., The New Royal Horticultural Dictionary of Gardening. vol. 4, p. 656. Jul. 10, 1999.*

* cited by examiner

*Primary Examiner*—Bruce R. Campell
*Assistant Examiner*—Michelle Kizilkaya
(74) *Attorney, Agent, or Firm*—James A. Lucas; Driggs, Lucas, Brubaker & Hogg Co, LPA

(57) ABSTRACT

This species of *Viburnum dentatum* turns brilliant red in October and maintains its red color late into November in USDA hardiness zone 5. In early June, it produces dense, flat white clusters of flowers, which last for 3 weeks. The shrub is very cold hardy and can withstand temperatures of −20° F.(−28° C.) without damage.

3 Drawing Sheets

BACKGROUND OF THE INVENTION

This invention relates to a Viburnum which is a product of open pollination of a seed parent *Viburnum dentatum* (unpatented) with an unidentified pollen parent. I first discovered this plant in a row of un-named *Viburnum dentatum* seedlings in a nursery in Plainsboro Township, N.J. in 1991. I asexually reproduced the plant by means of soft wood cuttings in a greenhouse in Plainsboro Twp. in New Jersey in 1993. I have observed the plants thus produced and find that the characteristics initially observed are in fact reproduced in successive generations.

The Viburnum family includes a varied and diversified group of shrubs grown for their ornamental value. They are appreciated for their white, cream and sometimes pink spring flowers, good foliage, interesting shape, their colored fruit which attracts birds, and their showy autumn color.

BRIEF SUMMARY OF THE INVENTION

The plant of this invention is characterized by turning brilliant red in October in USDA hardiness zone 4 and maintaining the red color into late November. The shrub is very cold hardy, having withstood temperatures down to −20° F. (−28° C.) without damage. The foliage is more brilliant and is longer lasting than that of the seed parent and other plants of the species.

DESCRIPTION OF THE DRAWINGS

This new variety of Viburnum is illustrated by the accompanying photographic drawings and depicts the plant by the best possible color representation using color photography. The color definitions in the specification have been taken from the Munsell Color Chart. While the colors depicted are believed to be of a high level of color fidelity, the coloration of this plant should be understood to be approximate and somewhat variable as a function of the cultural conditions and horticultural practices of the grower. For example, the leaf coloration may vary depending on the composition and the concentration of fertilizer that may be applied to the plant.

BOTANICAL DESCRIPTION OF THE PLANT

Figure 1:
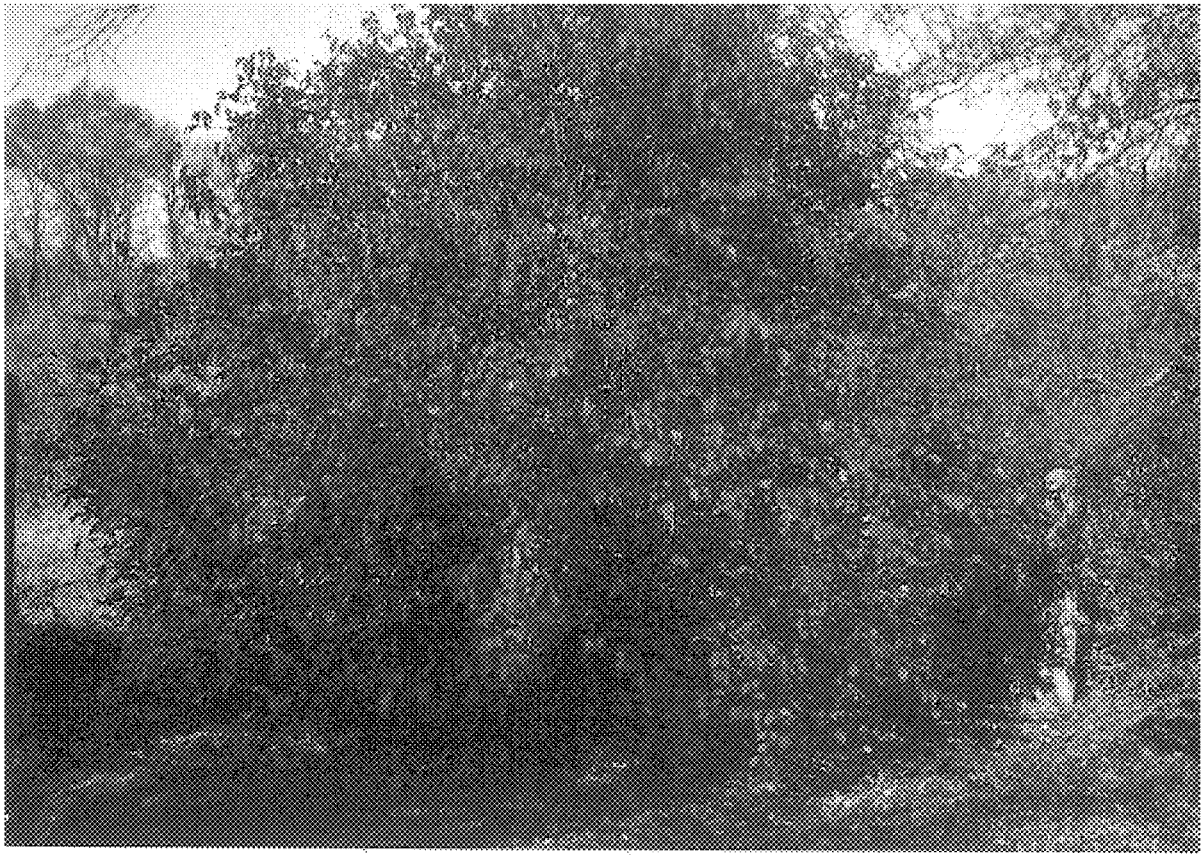
FIG. 1 is a view showing the entire tree.
Figure 2:
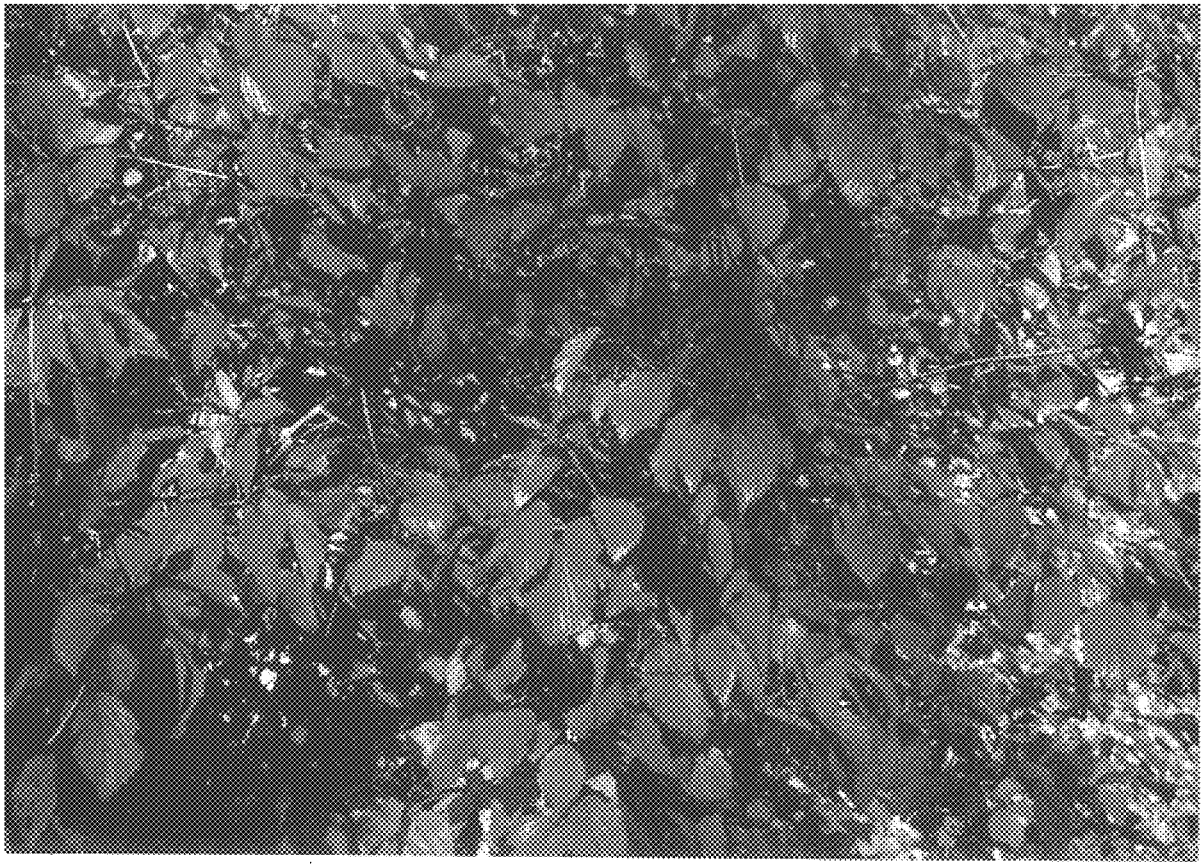
FIG. 2 is a view showing a close-up of the foliage.
Figure 3:
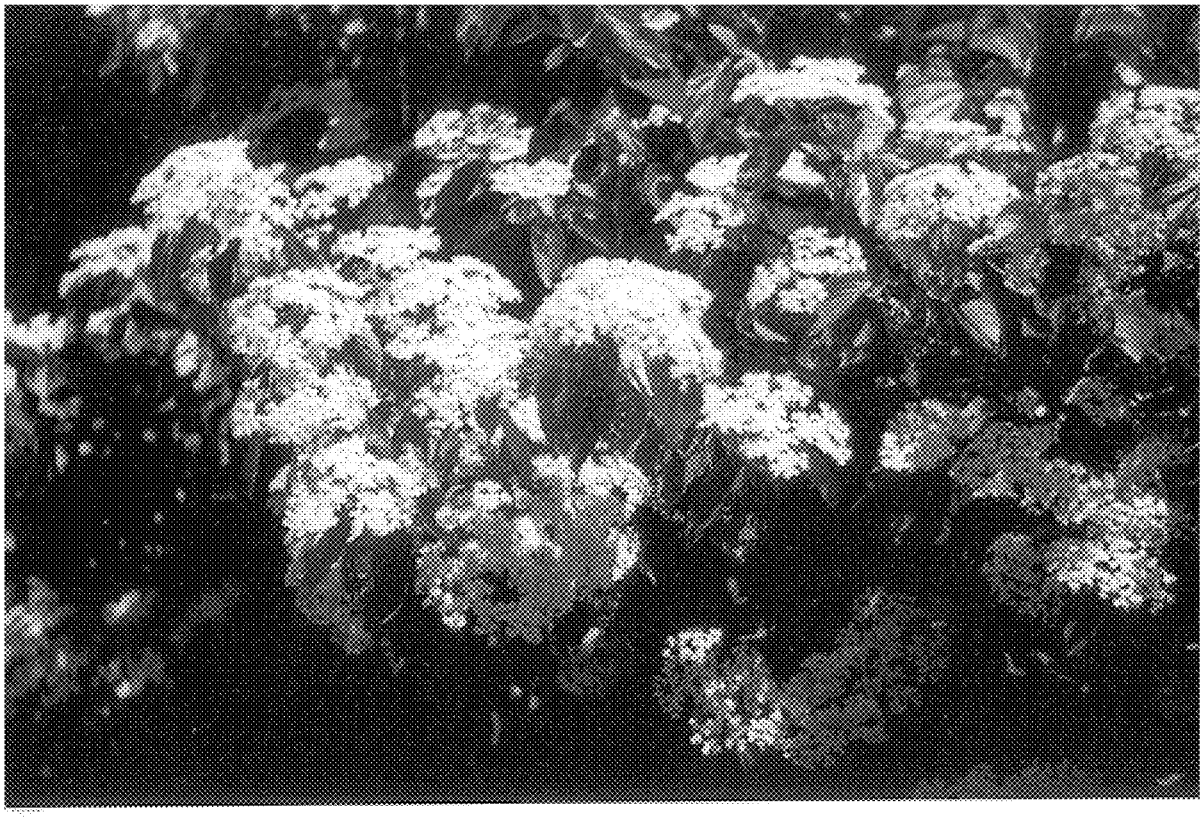
FIG. 3 is a view showing the flowers.

Shrub: Large, 2.5 meters tall and 3.4 meters wide; spreading; dense and hardy.
Main stems: Munsell Olive Gray 5Y 3/1.
Branches:
- *Slender.*—Smooth.
- *Color.*—Munsell Moderate Olive 5Y 4/3.
- *Lenticels.*—Sparse; Number: 4 to 5 per cm of stem.

Leaves:
- *Quantity.*—Abundant, with glabrous glossy upper surface.
- *Length.*—8 cm.
- *Width.*—5 cm.
- *Shape.*—Ovate, cordate base coarsely dentate, glabrous and shiny; 10 to 12 pairs of veins; Acuminate tips.
- *Color.*—Fall Color: Upper surface Munsell, Strong Red 5 SR 4/12. Lower surface Munsell Strong Reddish Brown 2.5YR 3/3.
- *Thickness.*—Medium.
- *Margin.*—Dentate.
- *Petiole.*—Long — 2 cm in length.
- *Glands.*—None exhibited.
- *Stipules.*—None.

Flower buds:
- *Hardiness.*—Very hardy.
- *Size.*—0.5 cm long, 0.2 cm across.
- *Shape.*—Narrow pointed.
- *Color.*—Dark red, Munsell Dark red 5 SR 3/7.
- *Number.*—Approximately 240 on young plants and approximately 550 on mature plants.

Flowers:

*Dates first bloom.*—June 1.

*Full bloom.*—June 15.

*Location.*—Princeton, N.J.

*Quantity.*—Normal. — Number varies depending on size and age of specimen; approximately 240 on young plants and approximately 550 on mature plants.

*Fragrance.*—None detectable.

*Sepals.*—None.

*Cymes.*—20–25 per compound cyme.

*Size.*—Small: Borne in flat, compound cymes, 7 to 8 cm across.

Petalage:

*Number of petals.*—5.

*Shape of petals.*—Ovate.

*Length.*—0.3 cm.

*Width.*—0.2 cm.

*Color.*—White.

Fruits: Globose, drupe borne in many-fruited flat cymose clusters, 55 to 65 fruits per cluster.

*When borne.*—September to late October.

*Abundance.*—Moderately abundant.

*Size.*—6 cm in diameter.

*Color.*—Blue-black-Munsell color chart Dark Blue 2.5 PB 3/6.

Reproductive organs:

*Stamens.*—5 in number; 0.3 cm. in length. Anthers: Number — Many. Size — Small. Arrangement — Regular around styles. Length — slightly longer than the corolla. Filaments: Threads — Short (0.28 cm. long). Color — Munsell pale orange yellow 7.5YR 9/4.

*Pollen.*—Each flower has an unquantifiable minute amount of pollen. Color — Munsell pale yellow 2.5Y 9/9.

*Pistil.*—One. Styles: Columnar; loosely separated; uneven. Size: Short length and thin. (0.32 cm. long). Stigmas: Color — Munsell 2.5 green yellow 9/8. Ovaries: All enclosed in calyx. Inferior.

Disease resistant: No disease observed.

What is claimed is:

1. A novel species of *Viburnum dentatum* shrub sustantially as shown and described herein.

* * * * *